United States Patent
Lidji

[19]

[11] Patent Number: 5,931,717
[45] Date of Patent: Aug. 3, 1999

[54] ABSORBENT BREAST PAD FOR NURSING MOTHERS

[76] Inventor: Shari R. Lidji, 7135 Fenton Dr., Dallas, Tex. 75231

[21] Appl. No.: 09/081,189

[22] Filed: May 19, 1998

[51] Int. Cl.[6] .............................. A41C 3/00; A41D 1/20; A61J 13/00; A61F 13/15

[52] U.S. Cl. ................................ 450/37; 2/104; 128/890; 604/358

[58] Field of Search .......................... 450/37, 36; 2/104, 2/267, 463; 128/890; 604/358, 367, 374, 378, 385.1, 386, 387, 388, 393

[56] References Cited

U.S. PATENT DOCUMENTS

| | | |
|---|---|---|
| 1,989,382 | 1/1935 | Schnaittacher . |
| 2,748,771 | 6/1956 | Richards . |
| 3,356,090 | 12/1967 | Plantinga et al. .................... 128/280 |
| 3,442,268 | 5/1969 | Bird . |
| 3,502,083 | 3/1970 | Howard et al. . |
| 4,047,534 | 9/1977 | Thomaschefsky et al. . |
| 4,074,721 | 2/1978 | Smits et al. . |
| 4,125,114 | 11/1978 | Repke . |
| 4,164,228 | 8/1979 | Weber-Unger ......................... 128/461 |
| 4,700,699 | 10/1987 | Tollerud et al. . |
| 4,875,492 | 10/1989 | Mitchell et al. . |
| 4,992,074 | 2/1991 | Diaz . |
| 5,017,174 | 5/1991 | Gowrylow .............................. 450/37 |
| 5,149,336 | 9/1992 | Clarke et al. ......................... 604/388 |
| 5,269,720 | 12/1993 | Moretz et al. . |
| 5,679,052 | 10/1997 | Rucki . |
| 5,683,286 | 11/1997 | Kielland . |
| 5,690,536 | 11/1997 | Madden et al. . |
| 5,843,062 | 12/1998 | Reidmiller . |

*Primary Examiner*—John J. Calvert
*Assistant Examiner*—Shirra L. Jenkins
*Attorney, Agent, or Firm*—Hitt, Chwang & Gaines, PC

[57] ABSTRACT

A washable or disposable nursing pad with an augmented lower region primarily for nighttime use comprising a first two to twenty layers of a washable absorbent fabric or a disposable paper-like sheet material with a second two to twenty layers of the same materials, but smaller in size than the first two to twenty layers of material, sewn in between on the lower region of the pad. The pad is large enough to cover substantially the entire female breast and to fill substantially the typical bra cup.

24 Claims, 4 Drawing Sheets

ABSORBENT BREAST PAD FOR NURSING MOTHERS

BACKGROUND OF THE INVENTION

1. Field of the Invention

The present invention relates generally to a device for absorbing breast milk leakage from the breasts of a nursing mother to prevent seepage into and through her garments. The invention is primarily for nighttime use when breast milk leakage is very substantial. The invention relates specifically to a washable or disposable oversized absorbent breast pad with an augmented lower region. The breast pad comprises a first plurality of layers of absorbent material plus a second plurality of layers of smaller size of absorbent material attached together in an off-center fashion.

2. Description of the Prior Art

Women who are breast feeding their children are presented with some problems unique to their condition. While production of the mother's milk begins shortly after childbirth, the quantity produced is initially unregulated. A period of time (several days to a few weeks) elapses during which the demands of the infant gradually influences the hormonal production of the mother which, in turn, adjusts the volume of milk produced. Two types of milk are produced by the human female breast: fore-milk and hind-milk. The majority of milk which nourishes the baby is called hind-milk and is produced during nursing. The breasts produce hind-milk at the rate demanded during the infant's feeding time. However, fore-milk is produced between feedings and may constitute a significant leakage problem to the mother. Especially during the initial adjustment period, the mother's breasts may produce a volume of milk too great for the infant's needs. Once milk production has adjusted to the needs of the child, fore-milk production continues regardless of the time of day or the fact that a feeding may have been missed.

Fore-milk production between feedings can result in leakage from the nipples. This problem is especially acute during the night. A nursing mother may also encounter the problem of excessive fore-milk production during the day when unable to express the milk or to breast feed the child. Because of variations in the human physiology, some women may simply experience overproduction of fore-milk between feedings and the associated leakage. Regardless of when leakage occurs, the woman's brassiere and her outer garment run the risk of staining, and she risks unnecessary embarrassment and discomfort.

Brassiere pad devices for absorbing breast milk leakage in nursing mothers are available on the market and fall into two general categories: disposable and re-useable pads. The primary disadvantage of existing pads on the market is inadequate absorbency, particularly during the night when the breasts continue to produce fore-milk while the mother sleeps. Although some of the pads currently on the market address the issue of adequate fluid capacity, the designs suffer from one or more other problems.

The United States Patent to Weber-Unger et al, U.S. Pat. No. 4,164,228, discloses a pad with an absorbing apron which is attached to a cap-shaped pad. The thickness of the material increases from the center of the cap-shaped portion to the apron. Although this pad addresses the need for greater absorption on the lower part of the pad, considering the effect of gravity on the fore-milk, the solution can create discomfort to the nursing mother. Since the thickened absorbing portion of this pad extends well below the breast it is positioned in the elastic brassiere band just below the breasts. The additional bulk in the brassiere band would make the brassiere tighter and therefore uncomfortable to the wearer. Additionally, as one skilled in the art would understand, the pressure of the brassiere band would limit the absorbent ability of that portion of the pad, restricting the fluid's ability to penetrate that area of absorbent material.

The United States Patent to Gowrylow et al, U.S. Pat. No. 5,017,174, discloses a pad with a small v-shaped portion of the pad for increased absorptive ability. The v-shaped area is created as a result of overlapping the fabric when folding it into a conical shape. The Gowrylow pad is primarily for use during the day because the conical shape is less conspicuous under clothing. However, the Gorylow pad would not effectively absorb nighttime leakage with the extra layers of fabric covering only a relatively small area.

The primary disadvantage of existing pads on the market is the general lack of absorbency, particularly during the night when the body continues to produce milk for the baby during sleeping hours. Although a number of nursing pads with multiple layers of various absorbent materials are available on the market, pads of the above mentioned type with the fortified lower region are not known.

Commercially available pads have other disadvantages, such as: (a) inadequate size for nursing breasts, and (b) single capacity absorbency, i.e., the "one size fits all" approach.

Therefore, a need exists for an improved nursing pad which is not susceptible to the above disadvantages and limitations.

SUMMARY OF THE INVENTION

One object of the present invention is to provide a nursing pad with greater absorbency. This is achieved by fortifying and augmenting the lower region of the pad with additional layers of absorbent material. The invention takes into consideration that milk leakage from the breast nipple will flow downward in accordance with the force of gravity and that greater absorption in this region is both necessary and desirable. The invention further addresses the economical conservation of materials by placing the bulk of the material only in the area in which it is most needed.

In one aspect, the present invention pertains to a nursing breast pad that has: (a) a first plurality of layers of a first absorbent material attached together; and (b) a second plurality of layers of a second absorbent material smaller in size than the first plurality of layers of the first absorbent material, wherein the second plurality of layers of the second absorbent material is attached to or within the first plurality of layers of the first absorbent material in an off-center fashion.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
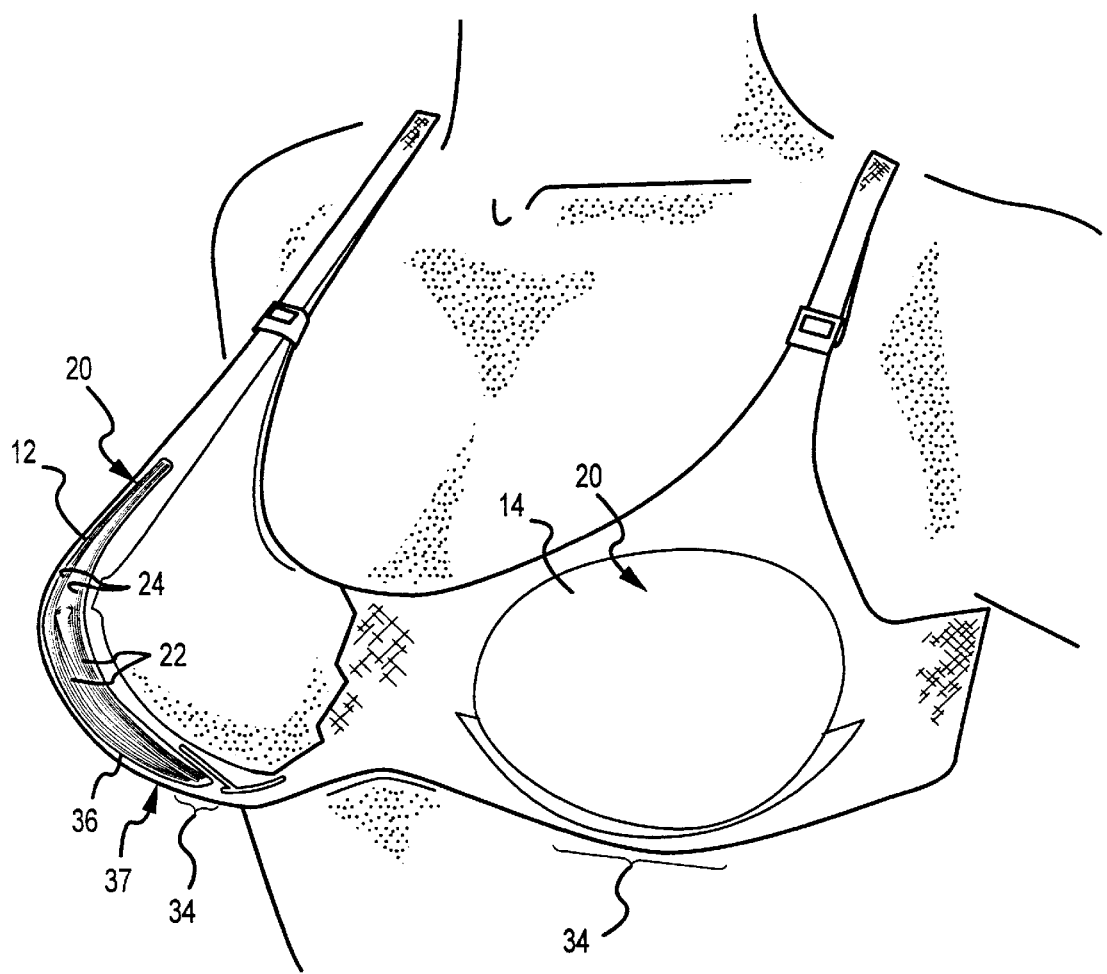
FIG. 1 illustrates a combined view of the breast pads contained within a brassiere, the left pad being in front view and the right pad being in cross section.

Referring initially to FIG. 1, which shows a frontal view of the nursing pads of one embodiment of the present invention. The figure shows a combined view of a pair of the breast pads contained within a brassiere; the left pad 14 being in front view and the right pad 12 being in cross section. The nursing pads, generally designated 20, are located within individual brassiere cups 34, and captured in place by the breast and brassiere cup 34. Referring to the front view of the left pad 14, the interchangeable pads 12, 14 are substantially circular in shape. Referring to the cross sectional view of the right pad 12, illustrated is a plurality of full circular and half-circular material layers forming laminated inner and outer surfaces 24 of the pad 20.

In a preferred embodiment, each of the right and left pads is of such a size that it will cover substantially the entire respective breast and will contact the majority of the inner surface 36 of the brassiere cup 34. By contacting the entire inner surface 36 of the brassiere cup 34, the pads 20 are less likely to shift within the brassiere. The fortified lower region corresponds to the generally rounded lower edge of the brassiere cup 34.

Figure 2:
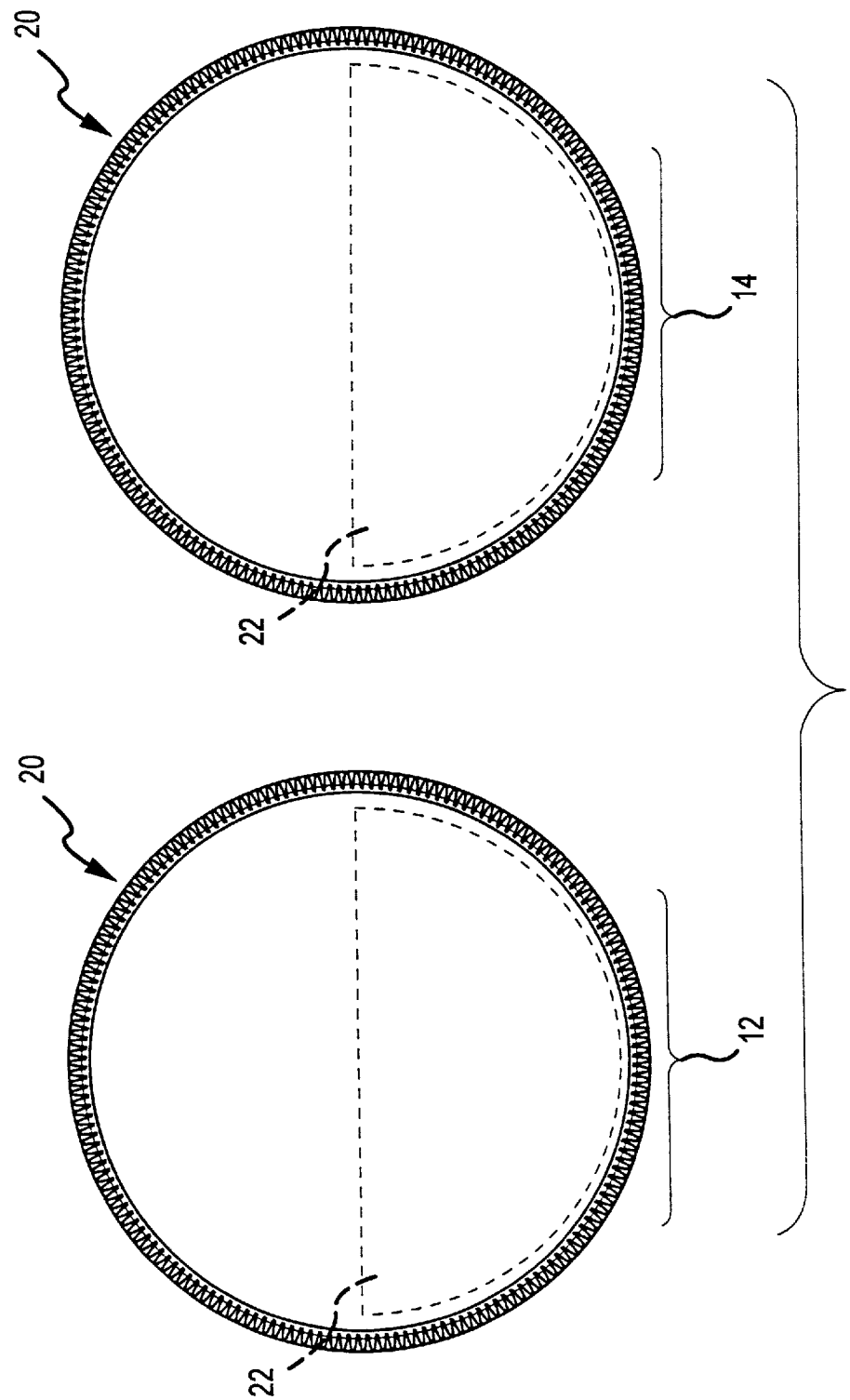
FIG. 2 illustrates a front plan view of the breast pads.

Turning now to FIG. 2, illustrated is a front plan view of the breast pads. The pads 20 are essentially circular in shape and are supplied in interchangeable pairs, a right pad 12 and a left pad 14; each pad large enough to cover the typical right or left breast. Dotted lines indicate the location of the augmenting, essentially half-circular layers 22 within the pads 20. The center of the circular pads 20 does not coincide with the center of the half-circular layers 22. They are "off center," in the sense that the two centers do not coincide. The arc on chord namely, one segment of the half circular circumference, of the half-circular layers 22 superimposes the circumference of the pads 20.

Figure 3:
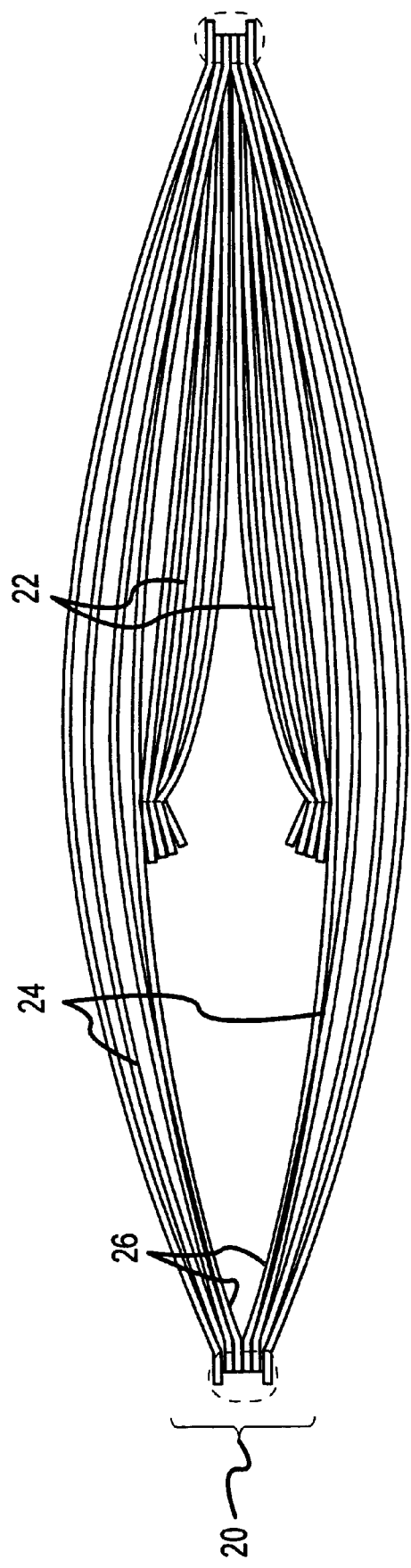
FIG. 3 illustrates a cross sectional view of the breast pad.

Turning now to FIG. 3, illustrated is a cross sectional view of the breast pad 20. The breast pad 20 is composed of a plurality, from two to twenty, of full circular layers 24 which, evenly divided, constitute the inner and outer surfaces of the breast pad 20. In the illustrated embodiment, the inner and outer laminates 24 consist of eight total plies of material. A plurality, from two to twenty, of substantially half-circular layers 22 are contained within the inner and outer full circular laminated layers 24 of the pad 20. In the illustrated embodiment, the half-circular layers 22 consist of eight total plies of material. A variety of embodiments consisting of from two to twenty full circular layers 24 and from two to twenty half-circular layers 22, provides necessary absorptive variability to the pads 20 to accommodate light to heavy leakage. While the described embodiment is that of a multi-layer pad of absorbent material, the multi layers may form an integral layer, thus one skilled in the art will recognize that a single layer pad may likewise be constructed of varying thicknesses and absorptive ability while remaining within the scope and intent of the present invention.

In the specific embodiment of the washable pad, the layers may consist of a washable material such as cotton flannel. In the specific embodiment of the disposable pad, the layers may consist of a material such as crepe-type paper. One skilled in the art will understand that the specific materials cited above are not a limitation to the invention in that a variety of materials may be substituted in a specific embodiment to achieve desired properties of washability, permeability, disposability, absorbability, etc.

Figure 4:
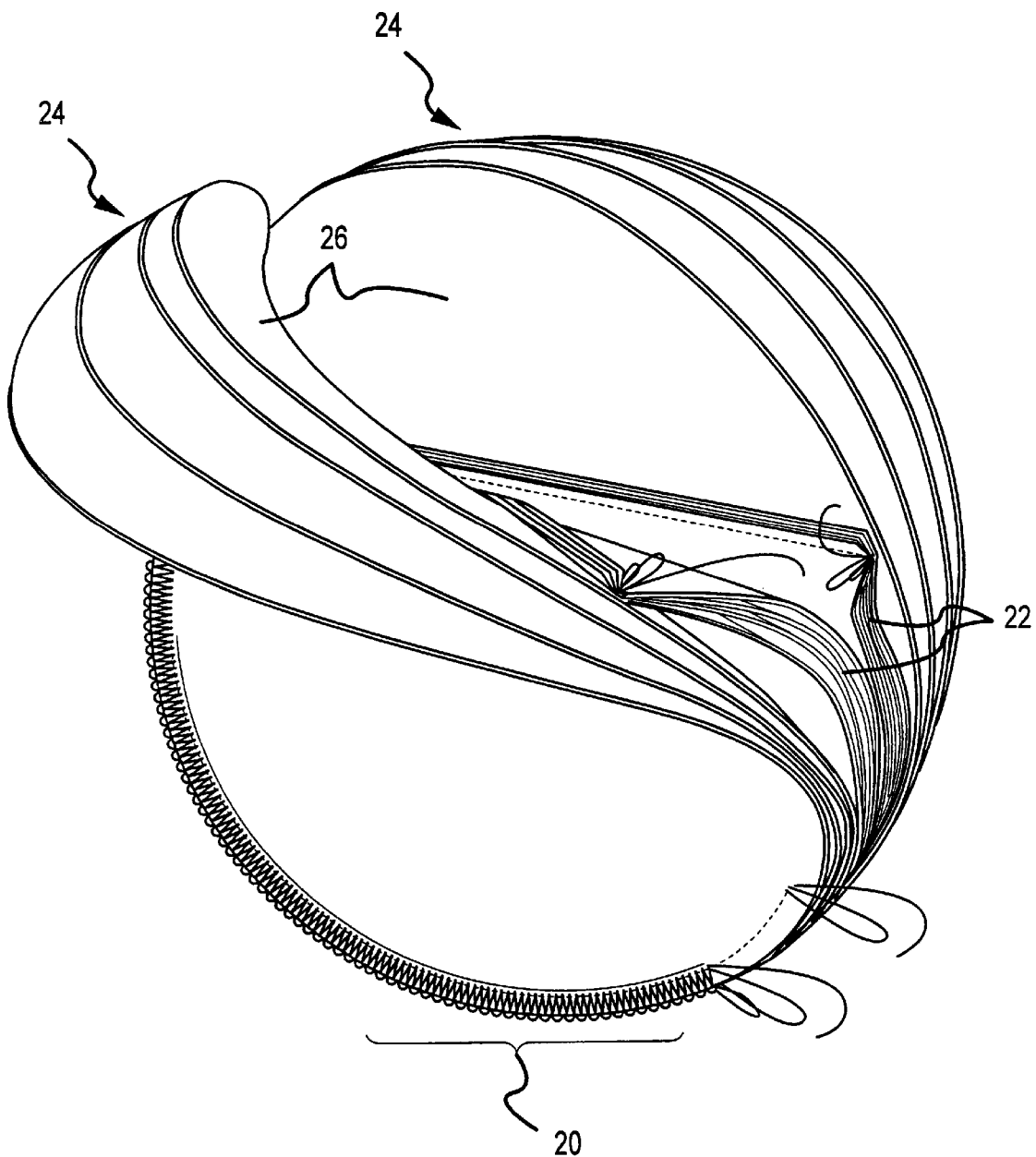
FIG. 4 illustrates an exploded mechanical drawing of the construction of the breast pad.

Referring now to FIG. 4, illustrated is an exploded mechanical drawing of the construction of the breast pad. Assembly of the nursing pads is as follows: the half-circular layers 22 are divided equally and sewn to one each of the innermost 26 full circular layers 24 across the center of the full circular layer 24. These two assemblies constitute the innermost parts of the pad 20. The remaining full circular layers 24 are then single needle stitched around the circumference of the pad 20. The pad 20 is completed with a serger stitch about the entire perimeter for additional strength.

In an alternative embodiment, the pads 20 are manufactured in cup sizes as in brassieres, i.e., A, B, C, D, etc. as well as various thicknesses to accommodate varying leakage problems.

In yet another alternative embodiment, the breast-side permeable non-absorptive layer is marked with permanent non-soluble ink such as: "This Side to Breast." In the alternative embodiment, especially of the light absorptive pad wherein confusion may be possible as to which portion is the augmented lower region, the breast-side permeable non-absorptive layer is additionally marked such as: "TOP" or "BOTTOM" as appropriate and desired.

A particular embodiment of the invention has been used to illustrate the same. The invention, however is not limited to the specific embodiment illustrated. In view of the foregoing disclosure, variations or modifications will be apparent and it is intended to include within the invention all such variations and modifications except as do not come within the scope of the appended claims.

What is claimed is:

1. A nursing breast pad comprising:
    a first plurality of layers of a first absorbent material attached together; and
    a second plurality of layers of a second absorbent material smaller in size than said first plurality of layers of said first absorbent material, wherein said second plurality of layers of said second absorbent material is attached to or within said first plurality of layers of said first absorbent material in an off-center fashion.

2. The nursing breast pad of claim 1, wherein said first plurality of layers of said first absorbent material is circular.

3. The nursing breast pad of claim 1, wherein said second plurality of layers of said second absorbent material is less than full circular.

4. The nursing breast pad of claim 1, wherein said first plurality of layers of said first absorbent material is circular having a full circular circumference and said second plurality of layers of said second absorbent material is semi-circular having an arc on chord.

5. The nursing breast pad of claim 4, wherein said arc on chord of said second plurality of said second absorbent material superimposes a portion of said full circular circumference of said first plurality of said first absorbent material.

6. The nursing breast pad of claim 1, wherein said first plurality of layers of a first absorbent material and said second plurality of layers of said second absorbent material are sewed together.

7. The nursing breast pad of claim 1, said first plurality of layers of a first absorbent material and said second plurality of layers of a second absorbent material comprise washable absorbent fabric.

8. The nursing breast pad of claim 1, said first plurality of layers of said first absorbent material and said second plurality of layers of said second absorbent material comprise disposable cellulose material.

9. The nursing breast pad of claim 1, wherein each of said first plurality of layers of said first absorbent material is about equal in size.

10. The nursing breast pad of claim 1, wherein each of said second plurality of layers of said second absorbent material is about equal in size.

11. A nursing breast pad comprising:
- a first plurality of layers of a near full circular first absorbent material attached together; wherein said first plurality of layers of said first absorbent material has a full circular circumference; and
- a second plurality of layers of a less-than-full circular second absorbent material, wherein said second plurality of layers of said second absorbent material has an arc on chord and wherein said second plurality of layers of said second absorbent material is attached to said first plurality of layers of said first absorbent material in an off-center fashion.

12. The nursing breast pad of claim 11, wherein said arc on chord of said second plurality of said second absorbent material superimposes a portion of said full circular circumference of said first plurality of said first absorbent material.

13. The nursing breast pad of claim 11, wherein said first plurality of layers of a first absorbent material and said second plurality of layers of said second absorbent material are sewed together.

14. The nursing breast pad of claim 11, said first plurality of layers of a first absorbent material and said second plurality of layers of a second absorbent material comprise washable absorbent fabric.

15. The nursing breast pad of claim 11, said first plurality of layers of said first absorbent material and said second plurality of layers of said second absorbent material comprise disposable cellulose material.

16. The nursing breast pad of claim 11, wherein each of said first plurality of layers of said first absorbent material is about equal in size.

17. The nursing breast pad of claim 11, wherein each of said second plurality of layers of said second absorbent material is about equal in size.

18. A nursing breast pad comprising:
- a first plurality of layers of about equal size of a circular first absorbent material attached together; wherein said first plurality of layers of said first absorbent material has a full circular circumference; and
- a second plurality of layers of about equal size of a semi-circular second absorbent material, wherein said second plurality of layers of said second absorbent material has an arc on chord and wherein said second plurality of layers of said second absorbent material is attached to said first plurality of layers of said first absorbent material such that said arc on chord of said second plurality of layers of said semi-circular second absorbent material superimposes a portion of said full circular circumference of said first plurality of layers of said circular first absorbent material.

19. The nursing breast pad of claim 18, wherein said first plurality of layers of a first absorbent material and said second plurality of layers of said second absorbent material are sewed together.

20. The nursing breast pad of claim 18, said first plurality of layers of a first absorbent material and said second plurality of layers of a second absorbent material comprise washable absorbent fabric.

21. The nursing breast pad of claim 18, said first plurality of layers of said first absorbent material and said second plurality of layers of said second absorbent material comprise disposable cellulose material.

22. The nursing breast pad of claim 18, wherein each of said first plurality of layers of said first absorbent material is about equal in size.

23. The nursing breast pad of claim 18, wherein each of said second plurality of layers of said second absorbent material is about equal in size.

24. A nursing breast pad comprising:
- a first plurality of layers of a circular first absorbent material sewed together; wherein said first plurality of layers of said first absorbent material has a full circular circumference; and
- a second plurality of layers of a semi-circular second absorbent material, wherein said second plurality of layers of said second absorbent material has an arc on chord and wherein said second plurality of layers of said second absorbent material is sewed to said first plurality of layers of said first absorbent material such that said arc on chord of said second plurality of layers of said semi-circular second absorbent material superimposes a portion of said full circular circumference of said first plurality of layers of said circular first absorbent material, wherein said first absorbent material and said second absorbent material comprise washable absorbent fabric.

\* \* \* \* \*